(12) United States Patent
Scott et al.

(10) Patent No.: US 11,312,614 B2
(45) Date of Patent: Apr. 26, 2022

(54) SYSTEM AND APPARATUS FOR REFILLING A RESERVOIR WITH LIQUID DISPENSED FROM A DISPENSER

(71) Applicant: Fontem Holdings 1 B.V., Amsterdam (NL)

(72) Inventors: Kenneth Scott, Lancashire (GB); Christopher Lord, Liverpool (GB); David Jones, Manchester (GB); Stephen J. McDonald, North Yorkshire (GB)

(73) Assignee: Fontem Holdings 1 B.V., Amsterdam (NL)

( * ) Notice: Subject to any disclaimer, the term of this patent is extended or adjusted under 35 U.S.C. 154(b) by 799 days.

(21) Appl. No.: 15/550,740

(22) PCT Filed: Feb. 5, 2016

(86) PCT No.: PCT/GB2016/050282
§ 371 (c)(1),
(2) Date: Aug. 11, 2017

(87) PCT Pub. No.: WO2016/128717
PCT Pub. Date: Aug. 18, 2016

(65) Prior Publication Data
US 2018/0044162 A1    Feb. 15, 2018

(30) Foreign Application Priority Data

Feb. 13, 2015  (GB) ..................................... 1502492
Mar. 26, 2015  (GB) ..................................... 1505216
Jan. 20, 2016  (GB) ..................................... 1601096

(51) Int. Cl.
*B67D 7/02*       (2010.01)
*A61M 11/04*    (2006.01)
(Continued)

(52) U.S. Cl.
CPC ......... *B67D 7/0294* (2013.01); *A61M 11/042* (2014.02); *A61M 15/06* (2013.01);
(Continued)

(58) Field of Classification Search
CPC ...... B67D 7/0294; B67D 7/0222; B67D 7/44; B67D 7/54; B67D 47/0833;
(Continued)

(56) References Cited

U.S. PATENT DOCUMENTS 490,915 A * 1/1893 Costigan .................... A47F 7/08
                                                    211/37
692,795 A * 2/1902 Moyle .................... F16L 37/252
                                                    285/81
(Continued)

FOREIGN PATENT DOCUMENTS

CA    2545907 A1   11/2007
EP    3100956 A2   12/2016
(Continued)

OTHER PUBLICATIONS

Japanese Patent Office; Notification of Reasons for Refusal in counterpart application No. 2017-542040; notification dated Aug. 23, 2018. Machine translation attached.
(Continued)

*Primary Examiner* — Timothy L Maust
*Assistant Examiner* — James R Hakomaki
(74) *Attorney, Agent, or Firm* — Dykema Gossett PLLC

(57) ABSTRACT

The present invention solves some of the problems of the prior art by providing a method, system and apparatus for readily refilling the reservoir of a smoking-substitute device with liquid from a dispenser. The method, system and apparatus of the present invention prevents liquid from being dispensed until the dispenser is securely and sealably engaged to the smoking-substitute device, provides inde-
(Continued)

pendent liquid and gas pathways between the dispenser and reservoir, and substantially alleviates the problems of spillage and/or leakage when dispensing liquid from the dispenser into the reservoir of the smoking-substitute device.

16 Claims, 19 Drawing Sheets

(51) Int. Cl.
| | |
|---|---|
| B05B 11/00 | (2006.01) |
| A61M 15/06 | (2006.01) |
| B65B 3/04 | (2006.01) |
| B65B 3/06 | (2006.01) |
| B65B 3/12 | (2006.01) |
| B65D 1/32 | (2006.01) |
| B65D 47/06 | (2006.01) |
| B65D 47/32 | (2006.01) |
| B67D 7/44 | (2010.01) |
| B67D 7/54 | (2010.01) |
| B65D 47/08 | (2006.01) |

(52) U.S. Cl.
CPC ...... B05B 11/0044 (2018.08); B05B 11/0097 (2013.01); B65B 3/04 (2013.01); B65B 3/06 (2013.01); B65B 3/12 (2013.01); B65D 1/32 (2013.01); B65D 47/06 (2013.01); B65D 47/32 (2013.01); B67D 7/0222 (2013.01); B67D 7/44 (2013.01); B67D 7/54 (2013.01); A61M 2209/045 (2013.01); B05B 11/0002 (2013.01); B65D 47/0833 (2013.01)

(58) Field of Classification Search
CPC ............... A61M 11/042; A61M 15/06; A61M 2209/045; B05B 11/0044; B05B 11/0097; B05B 11/0002; B05B 3/04; B65B 3/04; B65B 3/06; B65B 3/12; B65B 39/001; B65B 11/0002; B65D 1/32; B65D 47/06; B65D 47/32; B65D 47/0833; B65D 47/243; B65D 83/42; B65D 39/001; A24F 40/42; A24F 40/48; A24F 47/002; A24F 47/008; A24F 40/10; A24F 47/00; F16L 37/38; F16L 37/40
USPC ............ 141/351; 251/149.1, 149.6; 137/614, 137/614.1, 614.2, 614.3, 614.4, 614.5, 137/614.6
See application file for complete search history.

(56) References Cited

U.S. PATENT DOCUMENTS

| | | | | |
|---|---|---|---|---|
| 996,127 | A * | 6/1911 | Patnaude | B67D 3/0029 62/299 |
| 1,890,011 | A * | 12/1932 | Wirz | F16L 37/40 285/95 |
| 2,344,739 | A * | 3/1944 | Shaft | F16L 37/42 251/149.5 |
| 2,628,850 | A * | 2/1953 | Summerville | F16L 37/42 251/149.7 |
| 2,907,591 | A * | 10/1959 | Gulick | F16L 37/248 285/148.14 |
| 3,005,475 | A * | 10/1961 | Beall, Jr. | F16K 24/04 141/198 |
| 3,033,247 | A * | 5/1962 | Beall, Jr. | B67D 3/02 141/308 |
| 3,125,135 | A | 3/1964 | Boyer et al. | |
| 3,540,402 | A * | 11/1970 | Kocher | H01M 50/60 141/198 |
| 3,624,755 | A | 11/1971 | Lambert | |
| 4,176,694 | A * | 12/1979 | Dickerson | B67D 7/46 116/109 |
| 4,699,188 | A * | 10/1987 | Baker | B67D 3/00 141/18 |
| 4,758,023 | A * | 7/1988 | Vermillion | F16L 37/252 285/401 |
| 5,000,234 | A * | 3/1991 | Weiss | B67C 3/10 141/40 |
| 5,058,636 | A | 10/1991 | Simmel et al. | |
| 5,088,774 | A * | 2/1992 | Spiegelman | F16L 39/005 285/123.1 |
| 5,234,038 | A | 8/1993 | Mitchell et al. | |
| 5,249,611 | A | 10/1993 | Law | |
| 5,465,875 | A * | 11/1995 | Garnett | A01M 7/0092 134/166 R |
| 5,507,326 | A * | 4/1996 | Cadman | B67D 7/342 141/1 |
| 5,560,522 | A | 10/1996 | Clark | |
| 5,628,352 | A | 5/1997 | Gracyalny et al. | |
| 5,636,660 | A * | 6/1997 | Pfleiderer | A61J 1/2089 137/550 |
| 5,890,517 | A * | 4/1999 | Laible | F16L 37/35 137/614.04 |
| 6,079,823 | A * | 6/2000 | Droege | B41J 2/17523 347/85 |
| 6,086,561 | A * | 7/2000 | Kriesel | A61M 5/152 604/133 |
| 6,155,464 | A | 12/2000 | Vachon | |
| 6,322,207 | B1 | 11/2001 | Hall et al. | |
| 6,378,742 | B1 * | 4/2002 | Rohr | B67D 1/0835 222/482 |
| 6,544,246 | B1 * | 4/2003 | Niedospial, Jr. | A61J 1/2096 604/403 |
| 6,581,851 | B1 | 6/2003 | Murphy | |
| 6,637,430 | B1 | 10/2003 | Voges et al. | |
| 6,691,738 | B2 * | 2/2004 | Kuo | B67D 7/0288 137/588 |
| 6,729,504 | B2 | 5/2004 | Bougamont et al. | |
| 6,938,650 | B2 * | 9/2005 | Mitchell | B60T 17/222 141/285 |
| 7,040,511 | B1 | 5/2006 | Petit | |
| 7,086,431 | B2 * | 8/2006 | D'Antonio | B65B 3/003 141/330 |
| 7,178,702 | B2 | 2/2007 | Maas et al. | |
| 7,441,570 | B2 * | 10/2008 | Hagleitner | B67D 3/046 141/301 |
| 8,684,994 | B2 * | 4/2014 | Lev | A61J 1/2096 604/415 |
| 9,402,787 | B2 * | 8/2016 | Brem | A61J 1/2096 |
| 9,414,991 | B2 * | 8/2016 | Sanders | A61M 39/10 |
| 9,636,277 | B2 * | 5/2017 | Foshee | A61J 1/2089 |
| 9,795,166 | B2 * | 10/2017 | Liu | A24F 47/008 |
| 9,834,327 | B2 * | 12/2017 | De Rosa | A45D 34/00 |
| 10,160,590 | B2 * | 12/2018 | Wells | B65D 83/38 |
| 10,272,170 | B2 * | 4/2019 | Dubief | A61L 9/03 |
| 10,292,424 | B2 * | 5/2019 | Brammer | A24F 40/485 |
| 10,709,173 | B2 * | 7/2020 | Monsees | A61M 11/042 |
| 2003/0070726 | A1 * | 4/2003 | Andreasson | A61J 1/2096 141/329 |
| 2004/0025968 | A1 | 2/2004 | Allen | |
| 2004/0118936 | A1 | 6/2004 | Schram et al. | |
| 2007/0277902 | A1 | 12/2007 | Dieudonat et al. | |
| 2008/0149098 | A1 | 6/2008 | Bonney et al. | |
| 2009/0183744 | A1 | 7/2009 | Hayton et al. | |
| 2010/0084041 | A1 * | 4/2010 | Fehr | A61J 1/20 141/1 |
| 2010/0242975 | A1 | 9/2010 | Hearn | |
| 2011/0084474 | A1 * | 4/2011 | Paden | F16L 37/004 285/9.1 |
| 2011/0272938 | A1 * | 11/2011 | Lin | E03C 1/0403 285/330 |
| 2012/0067429 | A1 * | 3/2012 | Mosier | B65D 51/002 137/1 |
| 2012/0097711 | A1 | 4/2012 | Xianzhi et al. | |
| 2012/0167906 | A1 | 7/2012 | Gysland | |
| 2012/0234432 | A1 * | 9/2012 | Lamboux | A45D 34/02 141/2 |

(56) References Cited

U.S. PATENT DOCUMENTS

| | | | |
|---|---|---|---|
| 2013/0306665 | A1 | 11/2013 | Eberhardt et al. |
| 2014/0041753 | A1* | 2/2014 | Beranger ............ B05B 11/0056 141/18 |
| 2014/0102584 | A1* | 4/2014 | Lasnier ................ B67D 7/0294 141/18 |
| 2014/0261399 | A1 | 9/2014 | Murphy |
| 2014/0284921 | A1* | 9/2014 | van der Valk ........ F16L 37/248 285/312 |
| 2016/0050976 | A1 | 2/2016 | Righetti |
| 2017/0048930 | A1* | 2/2017 | Marsh ..................... H02J 50/10 |
| 2017/0064997 | A1* | 3/2017 | Murison ................. A24F 15/18 |
| 2017/0268709 | A1* | 9/2017 | Gibson ................. F16L 37/252 |
| 2018/0257797 | A1 | 9/2018 | Beer |

FOREIGN PATENT DOCUMENTS

| | | |
|---|---|---|
| EP | 3124430 A1 | 2/2017 |
| EP | 3143884 A2 | 3/2017 |
| EP | 3254987 A1 | 12/2017 |
| EP | 3348155 A1 | 7/2018 |
| GB | 921899 | 3/1963 |
| GB | 1579283 | 11/1980 |
| GB | 2512326 A | 10/2014 |
| GB | 2524296 A | 9/2015 |
| GB | 2531830 B | 7/2017 |
| JP | H02205503 A | 8/1990 |
| JP | 2000025779 A | 1/2000 |
| WO | 9406703 | 3/1994 |
| WO | 0017091 A1 | 3/2000 |
| WO | 2014195859 A2 | 12/2014 |
| WO | 2014199098 A1 | 12/2014 |
| WO | 2015059399 A1 | 4/2015 |
| WO | 2015157224 A1 | 10/2015 |
| WO | 2017024926 A1 | 2/2017 |
| WO | 2017071298 A1 | 5/2017 |

OTHER PUBLICATIONS

European Patent Office; Office Action issued in corresponding EP Application No. 16703943.9. dated Oct. 31, 2019.

SIPO; Notification of First Office Action in counterpart application No. 2016800101457; notification dated Jul. 1, 2019. translation attached.

State Intellectual Property Office of the P.R.C., Office action issued in related application No. 2016800214879. dated Oct. 8, 2019. (references cited in IDS filed Nov. 12, 2019.)

State Intellectual Property Office of the P.R.C., Office action issued in related application No. 201680021486. dated Dec. 4, 2019.

* cited by examiner

SYSTEM AND APPARATUS FOR REFILLING A RESERVOIR WITH LIQUID DISPENSED FROM A DISPENSER

TECHNICAL FIELD

The present invention relates to a system and apparatus for refilling a reservoir with liquid dispensed from a dispenser, In particular, but not exclusively, to a system and apparatus for the substantially leak-free refilling of the reservoir of a smoking-substitute device with a liquid comprising nicotine from a refill dispenser.

BACKGROUND

A smoking-substitute device is an electronic device that permits the user to simulate the act of smoking by producing an aerosol mist or vapour that is drawn into the lungs through the mouth and then exhaled. The inhaled aerosol mist or vapour typically bears nicotine and/or other flavourings without the odour and health risks associated with traditional smoking and tobacco products. In use, the user experiences a similar satisfaction and physical sensation to those experienced from a traditional smoking or tobacco product, and exhales an aerosol mist or vapour of similar appearance to the smoke exhaled when using such traditional smoking or tobacco products.

A smoking-substitute device generally uses heat and/or ultrasonic agitation to vaporize a solution comprising nicotine and/or other flavouring, propylene glycol and/or glycerine-based base into an aerosol mist of vapour for inhalation. A person of ordinary skill in the art will appreciate that the term "smoking-substitute device" as used herein includes, but is not limited to, electronic nicotine delivery systems (ENDS), electronic cigarettes, e-cigarettes, e-cigs, vaping cigarettes, pipes, cigars, cigarillos, vaporizers and devices of a similar nature that function to produce an aerosol mist or vapour that is inhaled by a user. Some electronic cigarettes are disposable; others are reusable, with replaceable and refillable parts.

Smoking-substitute devices typically resemble a traditional cigarette and are cylindrical in form with a mouthpiece at one end through which the user can draw the aerosol mist or vapour for inhalation. These devices usually share several common components: a power source such as a battery, a reservoir for holding the liquid to be vaporized, a vaporization component for atomizing and/or vaporizing the liquid and to thereby produce an aerosol mist and/or vapour, and control circuitry operable to actuate the vaporization component responsive to an actuation signal from a switch operative by a user or configured to detect when the user draws air through the mouthpiece by sucking or inhaling.

The reservoir may be either a replaceable or refillable container that is coupled to, or located in, the main body of the smoking-substitute device and that is typically made of a resilient plastic material such as high-density polypropylene. The reservoir generally contains a wicking material in which the liquid is stored but may just be a storage space without any wicking material. Once the replaceable or refillable reservoir is emptied it must either be replaced or refilled.

Replaceable type reservoirs are typically provided in the form of a pre-filled cartridge that can be securely and removably engaged to, or within, the cylindrical main body of the smoking-substitute device. These reservoir and vaporization elements may also be integrated into a single component commonly known as a "cartomizer" that may be disposable or refillable. Additionally, replaceable type reservoirs may also be integrally formed with the mouthpiece.

In order to fit a replaceable type reservoir to, or within, the main body of a smoking-substitute device, features of the main body are configured to engage with complementary features formed on a portion of the reservoir to securely and removably couple the reservoir to the main body of the smoking substitute device and to thereby prevent the accidental or unintended separation of the reservoir from the smoking-substitute device. These complementary features typically secure the reservoir to the main body of the smoking-substitute device with a close or interference fit and the fitting step causes a portion of the reservoir to pierce the reservoir to permit liquid to be dispensed.

Alternatively, and most commonly, users utilise refillable type reservoirs. Typically, the refillable reservoir of the smoking-substitute device is refilled by dispensing liquid from a dispenser that commonly resembles the small dropper bottles used for dispensing eye drops. Refill dispensers are preferred principally for their low cost.

The ingredients of the liquid for producing the aerosol mist or vapour in smoking-substitute devices vary widely, but typically include water and flavourings in a propylene glycol and/or glycerol base. Nicotine may also be included in solutions intended to fulfil a nicotine replacement role, without the harmful products associated with tobacco smoke.

A person of ordinary skill in the art will appreciate that the term "liquid" as used herein, may include, but is not limited to, any liquids, gels, powders and gases together with liquids comprising mixtures of liquids, gels, powders and gases that are capable of being atomized or vapourized whether or not using heat and/or ultrasonics.

When refilling the reservoir from a dispenser, the user typically drips liquid from the outlet liquid-dispensing tip of the dispenser into an inlet of the reservoir by squeezing the walls of the dispenser. Any wicking material in the reservoir then absorbs the dispensed liquid or the space in the reservoir is simply filled with the dispensed liquid. Since the diameter of the inlet on the smoking-substitute device is typically quite narrow it is important that the liquid-dispensing tip of the dispenser is correctly aligned to prevent spillage. Additionally, the user must correctly judge the pressure with which the dispenser should be squeezed to controllably expel liquid from the liquid-dispensing tip. Furthermore, as the user releases the bottle air is sucked in through the liquid-dispensing tip to replace the volume of liquid that has just been dispensed, but can also suck recently dispensed liquid from the reservoir and back into the dispenser causing droplets of liquid to be expelled inadvertently from the reservoir. Consequently, this refill technique is cumbersome and typically results in spillages of oily liquid, which has an oily consistency, and so some users have found that utilizing a syringe to draw liquid from the outlet of the dispenser before injecting it through the inlet of the reservoir is more convenient.

A method of refilling the reservoir of a smoking-substitute device from a dispenser is disclosed in US 2014/0283946 A1 (Kribs, et al). This published patent application describes a cap that fits over the liquid-dispensing tip of a standard eyedropper type refill dispenser. The cap has a first portion with a bore into which the liquid-dispensing tip of a standard bottle is received, and an inner annular wall that is threaded, such that a gap is disposed between the liquid-dispensing tip and the threaded portion of the inner annular wall. When liquid is to be dispensed into the reservoir to refill the reservoir, the first portion of the cap is screwed onto a reciprocal threaded outer portion of the smoking-substitute device. When fully engaged the first portion of the cap is substantially sealed against the inlet of the reservoir of the smoking-substitute device to permit liquid to flow between the dispenser and the reservoir and alleviate leakage.

The popularity and use of smoking-substitute devices has grown rapidly in the past few years. Although originally marketed as an aid to assist habitual smokers wishing to quit traditional smoking and tobacco products, consumers are increasingly viewing smoking substitute devices as desirable lifestyle accessories. This has caused concern that smoking-substitute devices may be becoming fashionable in certain sections of the population, and that their use may as a consequence be attractive to children and young adults who may subsequently graduate to traditional smoking and tobacco products.

There is also significant on-going scientific debate about the long-terms effects on health from the prolonged use of smoking-substitute devices and the inhalation of atomized mists and/or vapours comprising nicotine constituents. However, it is generally accepted that the levels of toxicants consumed by users of such smoking-substitute devices is a fraction of those consumed by users of traditional smoking and tobacco products. See, for example, John H. Lauterbach et al, "*Suggested Protocol for Estimation of Harmful and Potentially Harmful Constituents in Mainstream Aerosols generated by Electronic Delivery Systems (ENDS)*", presented at SOT, San Francisco, Calif., Mar. 10-16, 2012 cigtoxdoc.ehost-services113.com and hereby incorporated by reference.

Nonetheless, the health issues connected with the prolonged use of smoking-substitute devices is increasingly receiving negative press coverage and is the subject of much political debate. One area of particular concern is the quality and provenance of many liquids presently available of the market. Concerns raised, particularly by the medical profession, also focus on the lack of information available to consumers regarding the use of smoking-substitute devices and associated liquids that prevent them from making informed decisions regarding their use.

To address safety and quality concerns relating to traditional smoking and tobacco products, the World Health Organisation (WHO) published the Framework Convention on Tobacco Control (FCTC) in May 2003. The FCTC provisions are intended to regulate the sale and marketing of tobacco and tobacco-alternative products, the disclosure of information relating to such products, the packaging and labelling of such products, and the advertising of such products. These provisions are binding on the European Union (EU) and its' Member States who have adopted a set of guidelines for the implementation of the FCTC provisions by consensus during a series of subsequent conferences. Although, the FCTC did not anticipate the market for smoking-substitute devices, the governments of several Member States have decided that it would be appropriate to adapt the current legislation resulting from the FCTC and that relates to traditional smoking and tobacco products to incorporate such smoking-substitute devices.

In Europe efforts to adapt the existing legislation followed the publication of various reports and advice received from the Scientific Committee on Newly Identified Health Risks (SCENIHR) on smokeless tobacco products and tobacco additives. The European Parliament and Council of the European Union has proposed repealing Directive 2001/37/EC and replacing it with Directive 2014/40/EU on Apr. 3, 2014 (Tobacco Products Directive or TPD). Although still to be enacted into the national laws of the Member States of the EU and not expected to come into force until May 2016, the TPD proposes regulations applicable to smoking-substitute devices that will:

limit the risks of inadvertent exposure to nicotine by setting maximum sizes for refill reservoirs, containers, tanks, and cartridges (Article 20.3(a))

limit the concentration of nicotine in the liquid to 20 mg/ml (Article 20.3(b)).

prohibit the use of certain additives in the liquid (Article 20.3(c))

require that only high-purity ingredients are used in the manufacture of liquids (Article 20.3(d)).

require that all ingredients (except nicotine) do not pose a risk to human health in heated or unheated form (Article 20.3(e))

require that all smoking-substitute devices deliver doses of nicotine at consistent levels under normal conditions of use (Article 20.3(f))

require that all products include child and tamper-proof labelling, fasteners and opening mechanisms (Article 20.3(g)).

require that all products meet certain safety and quality standards and to ensure that products do no break or leak during use or refill (penultimate and final sentences, paragraph 41 of the recitals).

One area of particular concern to consumers and regulators is that the increased availability of smoking-substitute devices and refill liquids in supermarkets and other outlets may create a health risk particularly if they fall into the hands of children. Although these liquids typically comprise nicotine in concentrations of less than or equal to 3.6% of the liquid which is generally regarded as safe and merely a stimulant, Nicotine in much higher concentration has in the past been used as an insecticide and in concentrations of 50-100 mg can be harmful to humans. Nonetheless, solutions comprising nicotine are treated as toxic by postal services and carriers, and so appropriate precautions are required when handling and storing nicotine in bulk.

Aspects and embodiments of the invention were devised with the foregoing in mind.

BRIEF SUMMARY OF THE PRESENT INVENTION

The present invention solves some of the problems of the prior art by providing a method, system and apparatus for readily refilling the reservoir of a smoking-substitute device with liquid from a dispenser. The method, system and apparatus of the present invention prevents liquid from being dispensed until the dispenser is securely and sealably engaged to the smoking-substitute device, provides independent liquid and gas pathways between the dispenser and reservoir, and substantially alleviates the problems of spillage and/or leakage when dispensing liquid from the dispenser into the reservoir of the smoking-substitute device.

The system and apparatus include complementary or reciprocal engagement elements that comprise features formed respectively on the dispenser and main body of the smoking-substitute device for securably and sealably engaging said dispenser in liquid and gas communication pathway with the reservoir of the smoking-substitute device. The engagement elements are moveable between an unsecured and closed position in which liquid and gas communication pathways are restricted between a dispenser outlet and a reservoir inlet and a reservoir outlet and a dispenser inlet, and a secured and open position in which said engagement elements simultaneously opens a liquid communication pathway between said dispenser and said reservoir through the dispenser outlet and reservoir inlet and a gas communication pathway between said reservoir and said dispenser through said reservoir outlet and dispenser inlet.

The engagement elements close both the liquid communication pathway and the gas communication pathway as it is moved away from the secured position to disengage the dispenser and reservoir. In the open position, the system and apparatus permit liquid to be transferred through the liquid communication pathway, and for a substantially equivalent volume of gas to be expelled through the gas communication pathway. Furthermore, in a advantageous embodiment, in the open position, the system and apparatus are designed to maintain a substantially equal pressure in the dispenser and reservoir.

The dispenser outlet preferably includes a valve that is actuable when the engagement elements are secured in the open position to open said liquid communication pathway between said dispenser and said reservoir. Similarly, the reservoir inlet preferably includes a valve that is actuable when the engagement elements are secured in the open position to open said gas communication pathway between said reservoir and dispenser. The valve assembly may be biased to close the gas communication pathway when the coupling assembly is not secured in the open position.

The coupling valve assembly preferably includes a guide assembly for guiding movement of the dispenser outlet into the secured and open position. The coupling assembly comprises a male member, and a female member configured for securely and removably receiving said male member. Various alternative configuration of the coupling assembly are suitable, including a bayonet-type arrangement, a magnetic-type arrangement, a screw-type arrangement, a slide-type arrangement, a friction-fit-type arrangement, and a speed-fit type arrangement.

The features and advantages of embodiments of the present invention will be more fully understood and appreciated upon consideration of the following detailed description and accompanying drawings, which set forth illustrative embodiments in which the concepts of the invention are utilized.

BRIEF DESCRIPTION OF THE DRAWINGS

A complete understanding of the present invention may be obtained by reference to the accompanying drawings, when considered in conjunction with the subsequent, detailed description, provided by way of example only and in which.

DETAILED DESCRIPTION OF THE INVENTION

Before the invention is described in further detail, it is to be understood that the invention is not limited to the particular embodiments described, as such may, of course, vary. It is also to be understood that the terminology used herein is for the purpose of describing particular embodiments only, and not intended to be limiting, since the scope of the present invention will be limited only by the appended claims.

Unless defined otherwise, all technical and scientific terms used herein have the same meaning as commonly understood by one of ordinary skill in the art to which this invention belongs or as determined by the context in which they are used. Although any methods and materials similar or equivalent to those described herein can also be used in the practice or testing of the present invention, a limited number of the exemplary methods and materials are described herein.

It must also be noted that as used herein and in the appended claims, the singular forms "a", "an", and "the" include plural referents unless the context clearly dictates otherwise. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, if dates of publication are provided, they may be different from the actual publication dates and may need to be confirmed independently.

The disclosure herein is directed to systems and apparatus for refilling a liquid reservoir from a refill dispenser and has particular applicability to the filling and refilling of the refillable reservoirs of smoking-substitute devices.

Figures 1, 2:
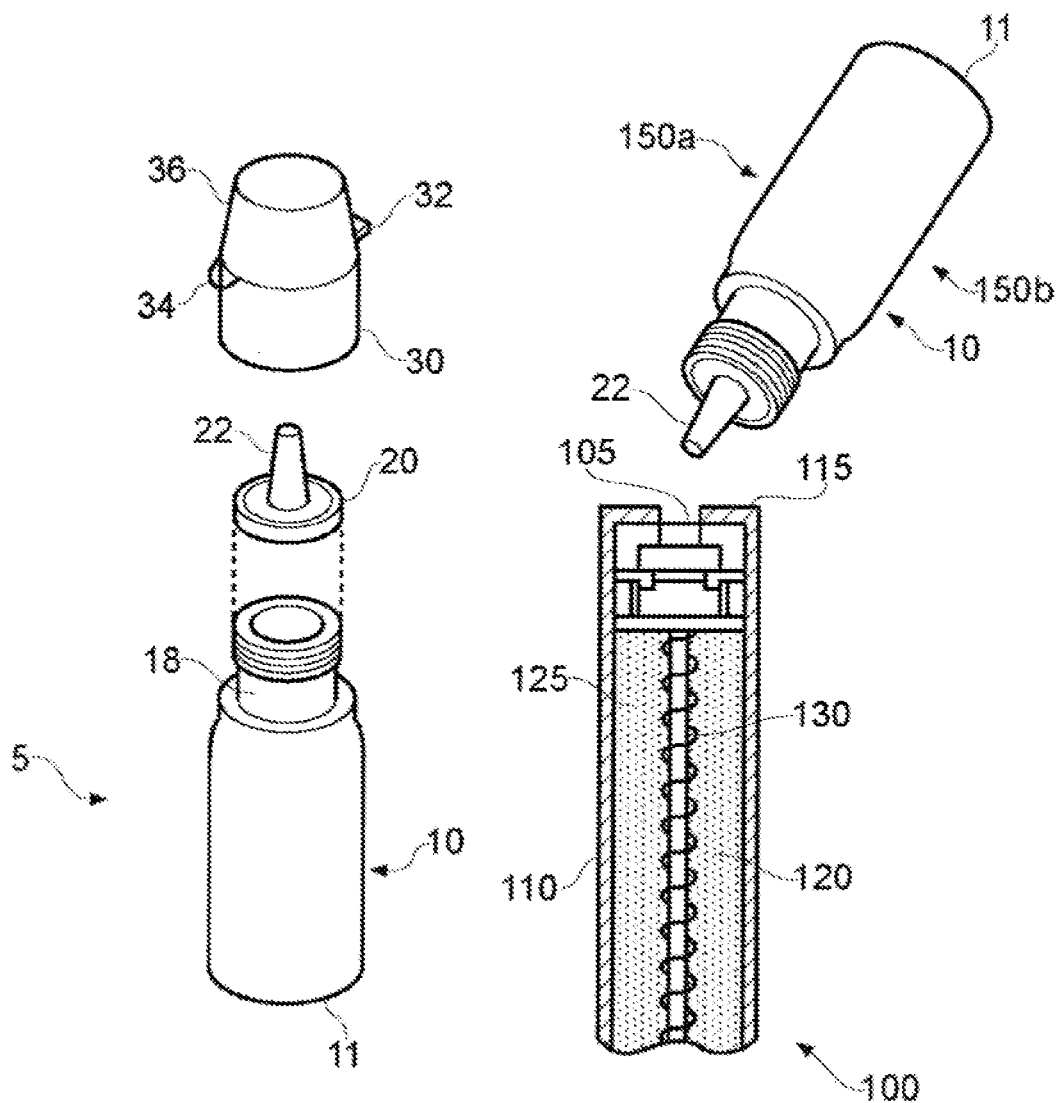
FIG. 1 is an exploded perspective view illustration showing a prior art liquid dispenser of the type typically used for refilling the reservoir of a smoking-substitute device.
FIG. 2 is an exploded perspective view illustration showing a liquid dispenser of the type described in connection with FIG. 1 being used to dispense liquid into the reservoir of a smoking-substitute device.

FIG. 1 shows an eyedropper type liquid dispenser 5 of the type presently used for refilling smoking-substitute devices. The liquid dispenser 5 includes a container 10, a dispensing portion 20 that comprises a liquid-dispensing tip 22, and a cap portion 30 that may be integrally formed with the neck portion 18 of the dispenser 10, the dispensing portion 20, or removable. As illustrated in FIG. 1, the cap portion 30 is removable and has a hinged portion 32 for permitting the lid portion 36 to be opened about the hinge portion 32 to expose the liquid-dispensing tip 22. Also illustrated is projection 34 which is provided to facilitate easy opening of the lid portion 36 by the user and when in the closed position prevents leakage from the liquid-dispensing tip 22.

Referring now to FIG. 2, a liquid dispenser 10 of the type described in relation to FIG. 1 is shown, together with a cross-sectional view of a portion of the body 110 of a smoking-substitute device 100 in which a reservoir 120 is located. The smoking-substitute device illustrated in FIG. 2 is of the type where access to the reservoir 120 is afforded by removing the mouthpiece (not shown) and the reservoir 120 is integrally formed with the vaporization chamber. Thus, the reservoir 120 is typically located in the proximal end 115 to the mouthpiece (not shown) and comprises a coiled heating element 130.

The reservoir 120 contains wicking material 125 for holding the liquid. The outer walls of the reservoir 120 are typically formed from a plastic material such as high-density polypropylene.

Before attempting to refill the smoking-substitute device the user must first remove the mouthpiece to provide access to the inlet aperture 105 of the reservoir 120. The user typically holds the smoking-substitute in an orientation in which its proximal end (i.e. the mouthpiece end) is uppermost. Although the smoking-device does not necessarily need to be vertical and slight inclination is possible to facilitate refilling, and indeed slight inclination can aid refilling, angles greater than around 20 degrees from the vertical can result in spillage.

Refill dispenser 10 is shown held at an angle of approximately 45 degrees from the vertical with the liquid-dispensing tip 22 disposed in the vicinity of the inlet aperture 105 of the smoking-substitute device so that any droplets expelled therefrom would fall generally in the region of such inlet aperture 105. Users typically find refilling of the reservoir 120 of a smoking-substitute device to be easier if the dispenser is held at an angle as their view of the liquid-dispensing tip 22 is not restricted by the body of the dispenser 10.

In use, the user will hold the refill dispenser 10 in an inverted orientation and a droplet of liquid typically forms at the end of the liquid-dispensing tip 22. Any volume in the body of the dispenser 10 that is not filled with liquid is typically air, which naturally rises to the bottom 11 of the dispenser 10 when it is disposed a substantially inverted orientation. To dispense liquid from the tip 22 the user squeezes the body of the bottle by applying pressure in the direction of arrows 150a and 150b causing the liquid to be expelled from the end of the tip 22. Furthermore, the walls of the dispenser in the region adjacent the arrows 150a and 150b may be inwardly deformed resulting in a reduction of the internal volume of the dispenser 10. Since the dispenser is typically moulded from a resilient plastic material, as the user releases the inwardly directed pressure applied to the walls of the dispenser 10 they return to their normal position. Consequently, as a volume of liquid has been dispensed from the dispenser 10 into the reservoir 120 the vacant volume will be replaced with air drawn through the tip 22.

Figure 18:
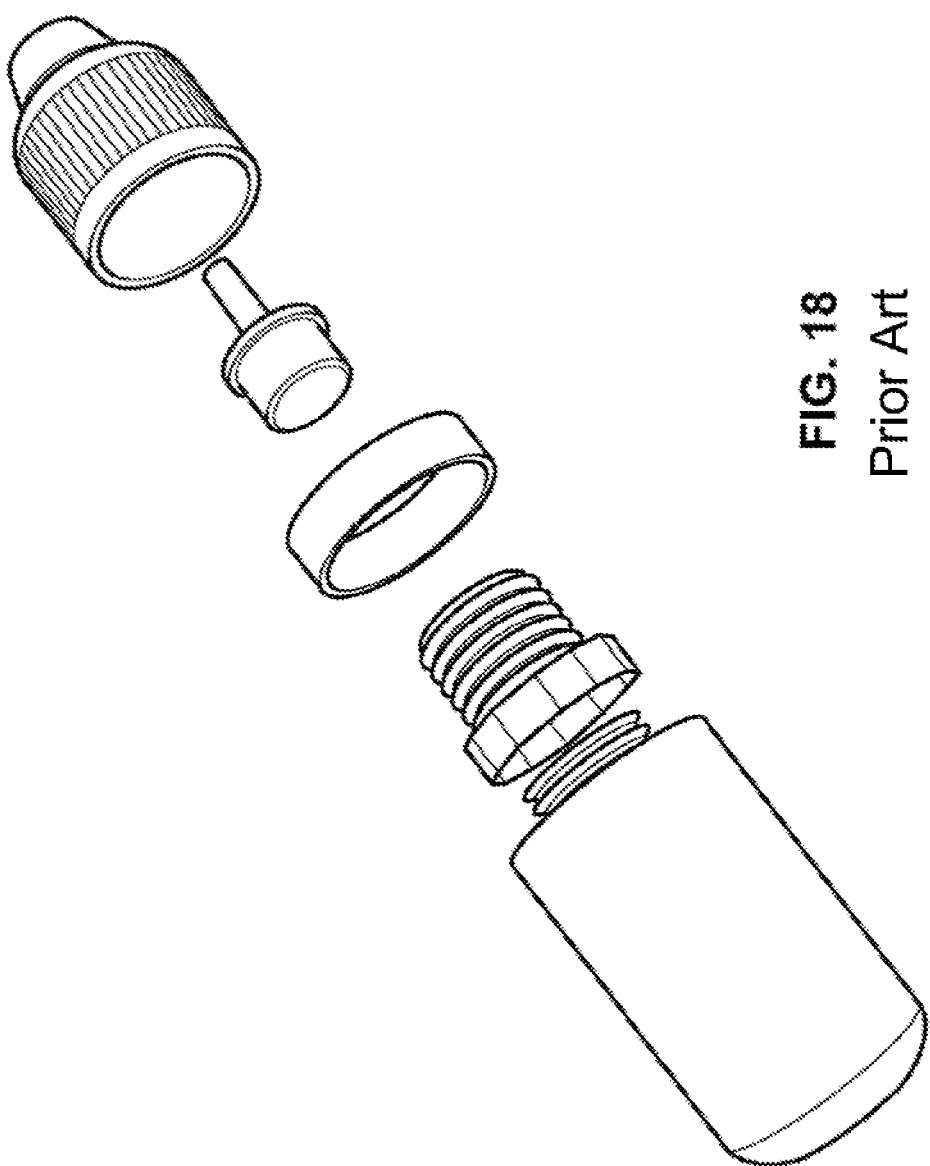
FIG. 18 is a schematic exploded view illustration of a prior art dispenser bottle.
Figure 19:
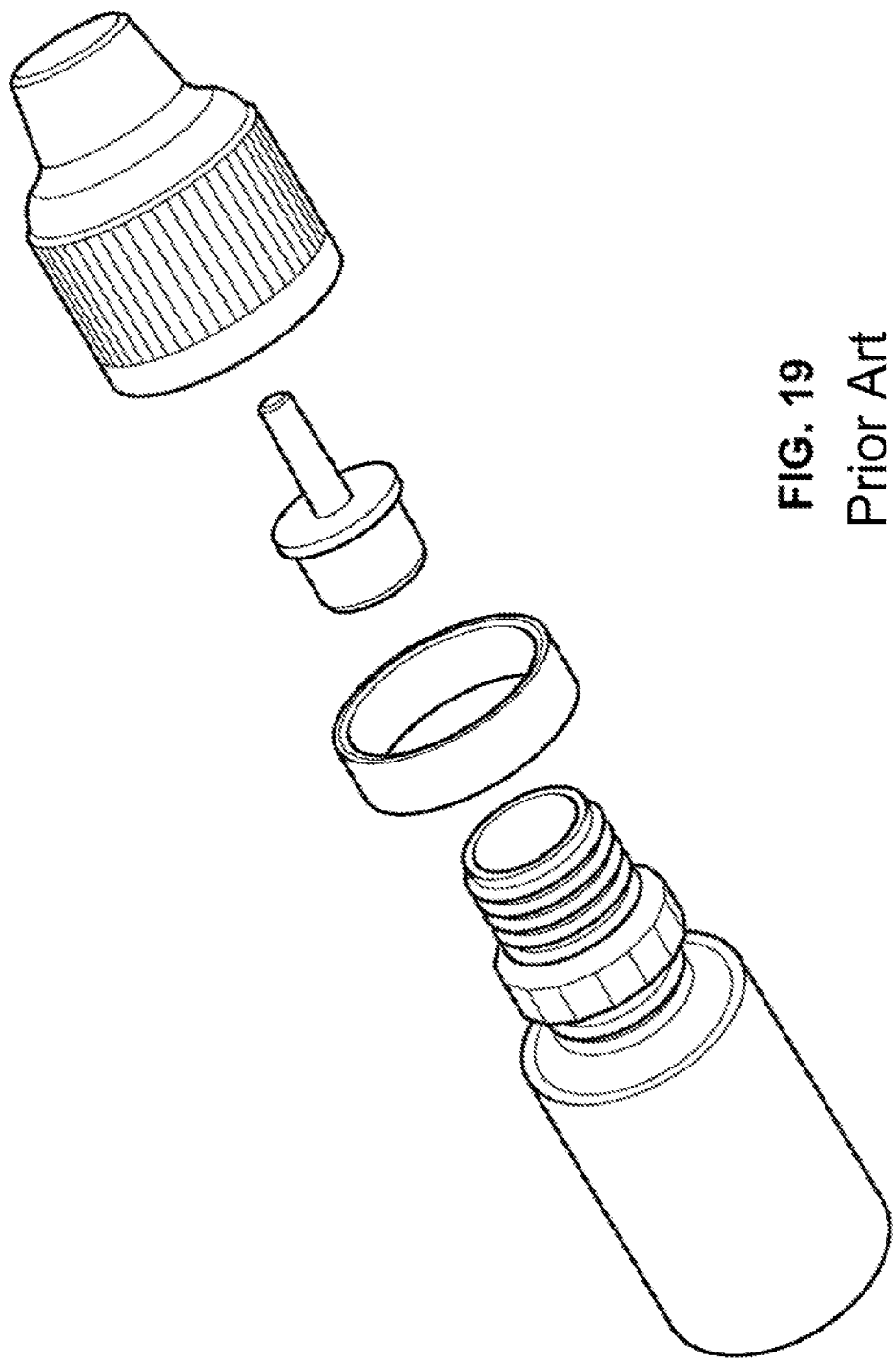
FIG. 19 is a schematic exploded view illustration of another prior art dispenser bottle.
Figure 20:
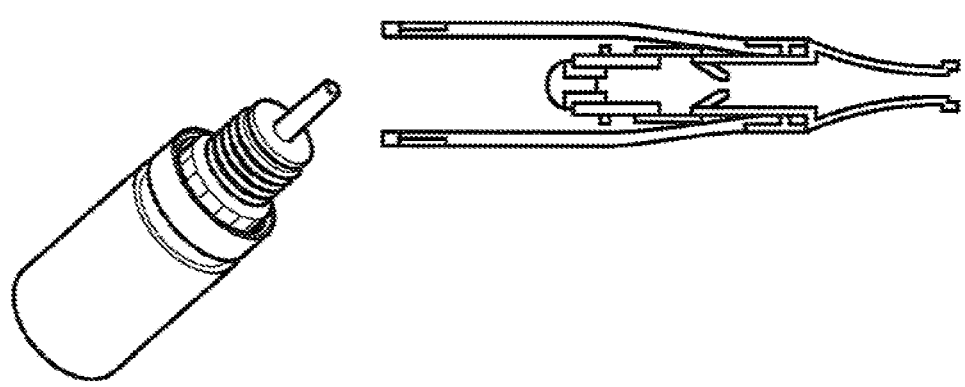
FIG. 20 is a cross-section view of a known e-cigarette being filled from a dispenser bottle.

Other known dispensers are illustrated in FIGS. 18 and 19. FIG. 20 illustrates in cross-section a known e-cigarette being filled from a dispenser bottle.

Figure 3:
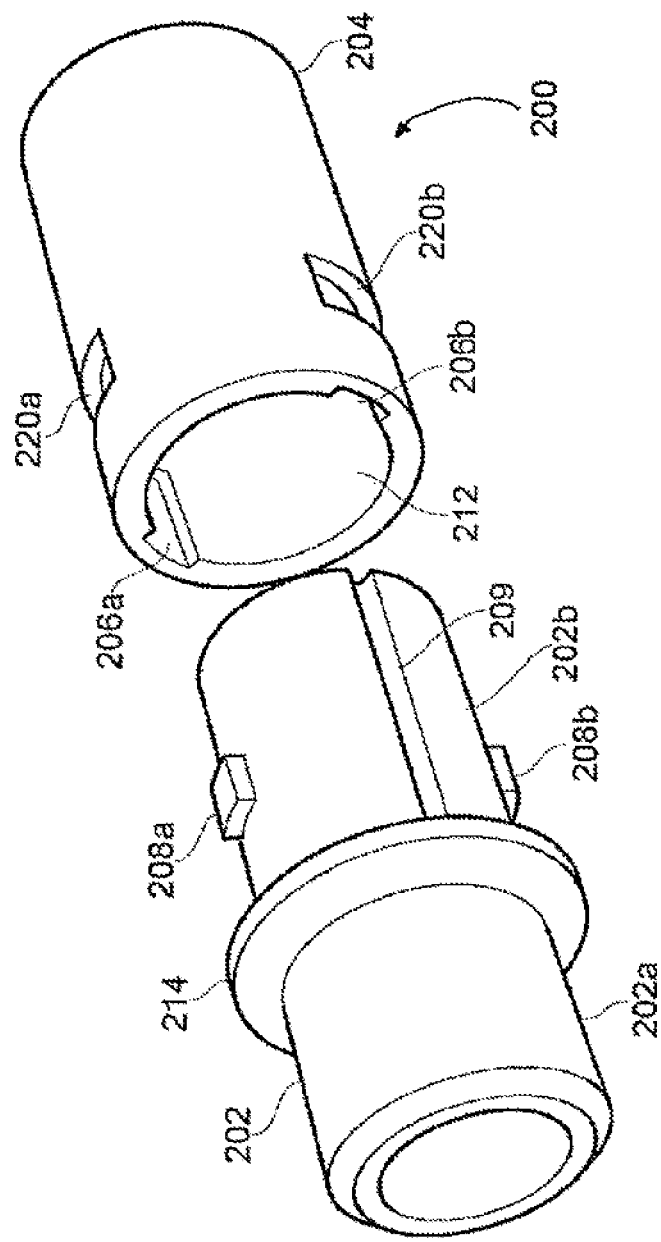
FIG. 3 is a perspective view illustration of the main features of the male and female components of apparatus in accordance with the present invention.

Turning now to FIG. 3, a perspective view of a disengaged coupling valve assembly 200 in accordance with an embodiment of the present invention is illustrated. The valve assembly comprises two main components, a male valve component 202 and a female valve component 204. The female component 204 forms a hollow cylinder and has grooves 206a and 206b formed in the interior wall of the cylinder. The grooves 206a and 206b are configured to receive tongues 208a and 208b respectively and grooves 206 and tongues 208a and 208b cooperate to guide the male component 202 into engagement with the female component 204 through cavity 212. The exterior wall 210 of the male component 202 is slideably engaged with the interior wall of the hollow cylinder forming the female component 204 other than in the region of the wall comprising groove 209.

The male component 202 comprises a flange 214 formed to provide a convenient abutment of two parts, 202a and 202b, of the male component 202 which are manufactured as separate units to allow for assembly of the other elements of the male components 202 as will be evident from the later description.

The female component 204 also includes slots 220a and 220b which are in respective communication with grooves 206a and 206b to receive tongues 208a and 208b respectively. Slots 220 extend in a circumferential direction and are shaped to provide a locking function by having a barrier around which a tongue may be moved against a bias. When the tongue has been moved around the barrier the bias returns it to a position in the slot such that the barrier inhibits the tongue returning back through the slot thereby inhibiting a twisting or rotational motion of the male and female components one with respect to the other.

Figure 4:
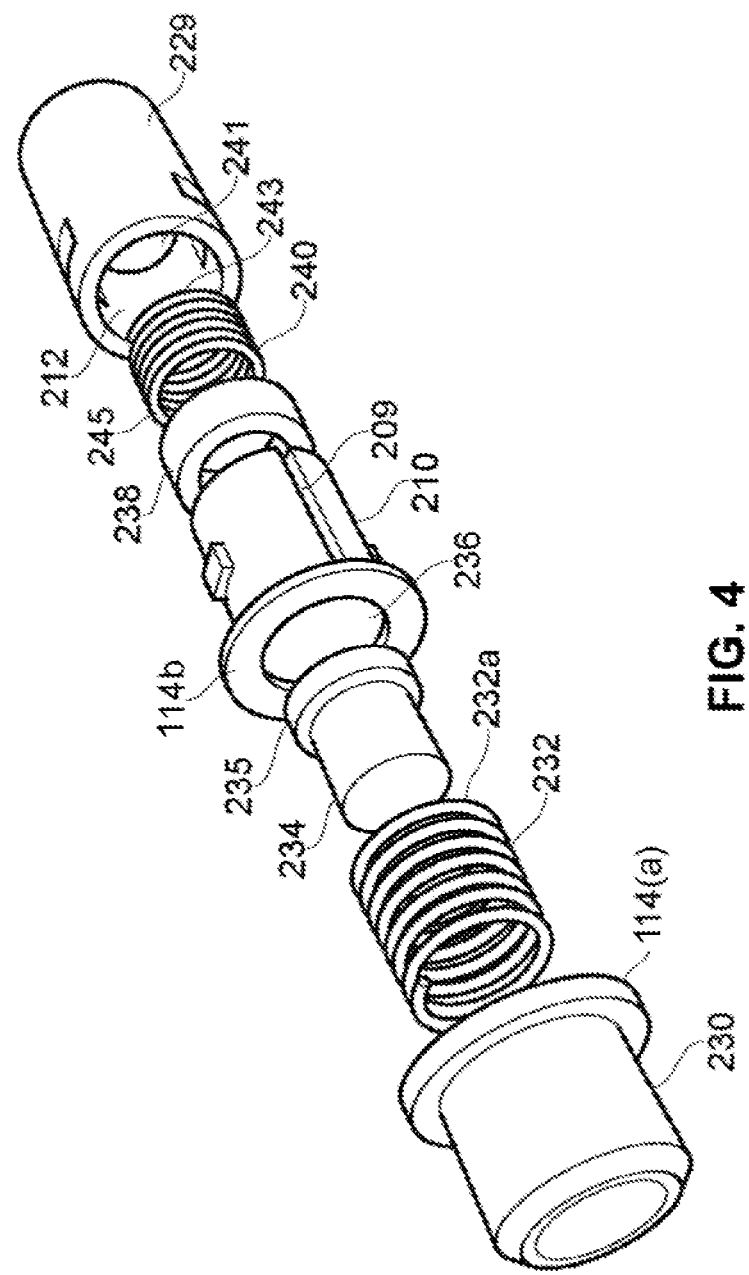
FIG. 4 is an exploded perspective view illustration showing the male and female components of apparatus in accordance with the present invention.

Referring now to FIG. 4, the two part configuration of male component 202 is clearly illustrated and comprises plunger guide 210 and an end cap 230. The plunger guide 210 has a flange 114b and end cap 230 has a flange 114a which facilitates joining respective parts, plunger guide 210 and end cap 230, together. A helical coil spring 232 is inserted into the end cap 230 and a plunger 234 extends through the middle of helical coil spring 232 so that a shoulder 235 on the plunger 234 may contact end 232a of the spring 232. The plunger 234 is inserted into the hollow cylindrical cavity 236 of part 210 of the male component. The respective parts of male component 202 may then be assembled.

Female component 204 comprises a main hollow cylinder 229, a collar 238 and second helical coil spring 240. The collar 238 and spring 240 are slideably insertable into the cavity 212 of the hollow cylinder 229 of the female component 204. A stopper 241 protrudes from an end of cylinder 229 distal from the end into which the spring 240 and collar 238 are inserted into the cylinder 229. The spring fits around stopper 241 and the distal end, 243, of the spring engages with an end wall (not shown) of the cylinder 229 of the female component 204. The proximal end, 245, of spring 240 engages with collar 238.

Figure 5:
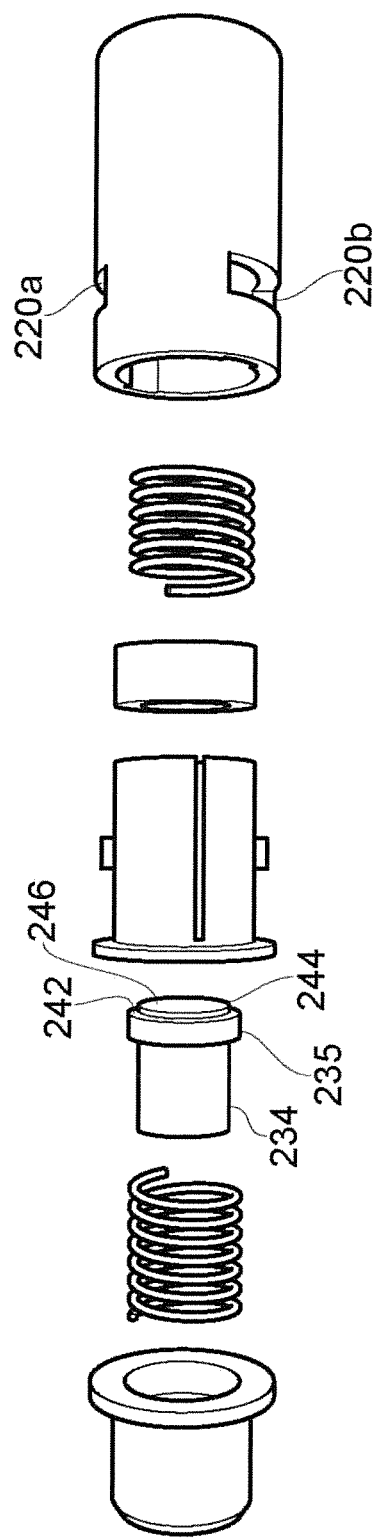
FIG. 5 is an exploded perspective view illustration showing the male and female components of apparatus in accordance with the present invention from a different aspect.

FIG. 5 is an illustration of an exploded view of the valve assembly from another aspect showing plunger 234 and details of the shoulder 235. Shoulder 235 includes an engagement surface 242, a neck 244 extending from the engagement surface and plunger head 246.

Figure 6:
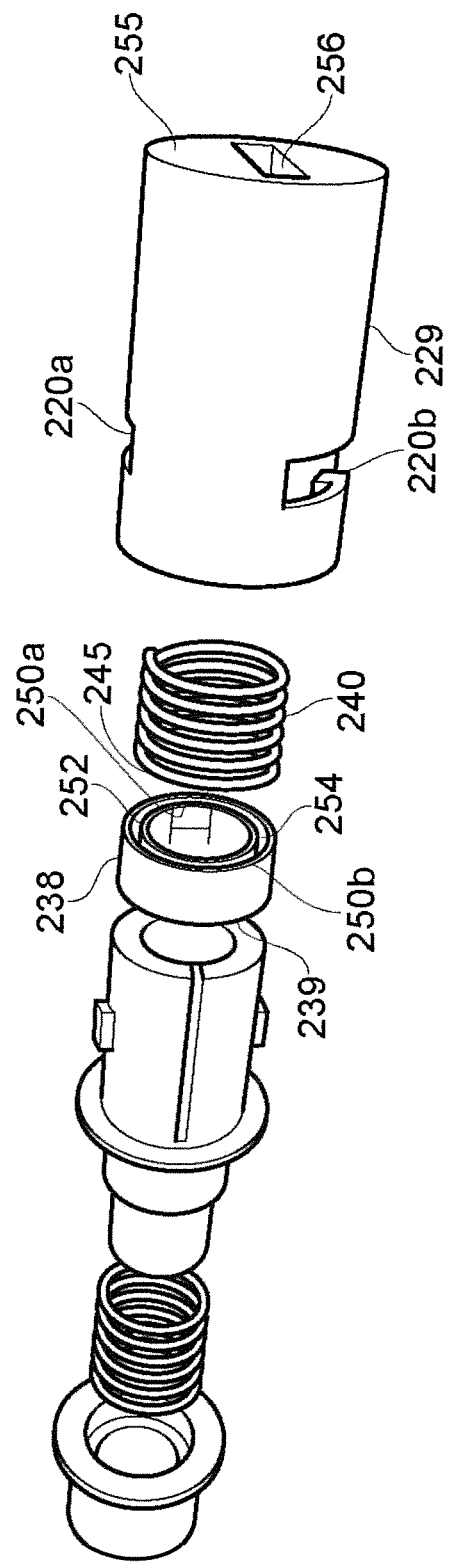
FIG. 6 is an exploded perspective view illustration showing the male and female components of apparatus in accordance with the present invention from a further different aspect.

An exploded view of the valve assembly from a yet another aspect is illustrated in FIG. 6 and shows details of collar 238. Collar 238 comprises a cylindrical groove 254 which on an inner wall 252 supports diametrically opposed catch members 250a and 250b. Distal end 245 of spring 240 is configured to be insertable into groove 254 and abut against the end wall 239 of collar 238. Hollow cylinder 229 is also shown having an end wall 255 with a cavity 256 which forms a pathway for liquid into the interior of cylinder 229.

Figure 7:
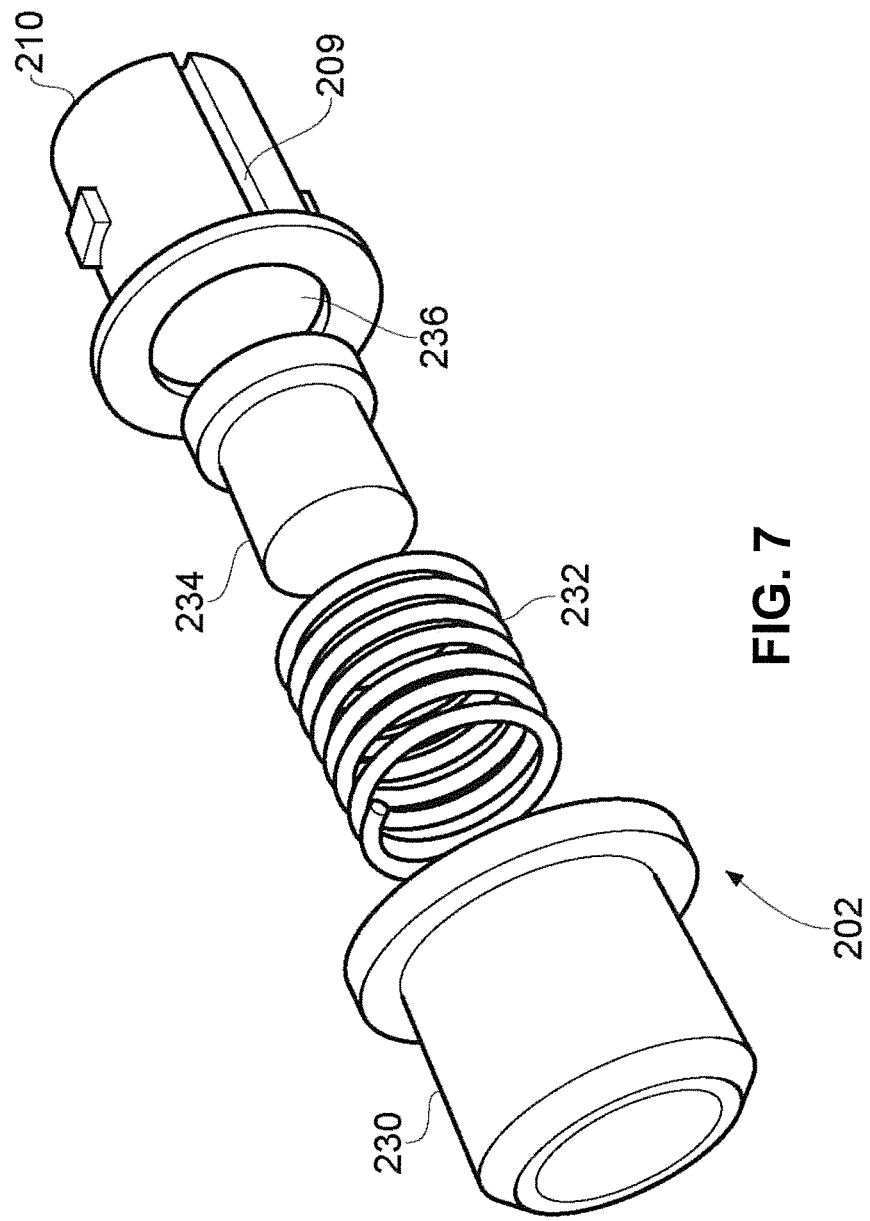
FIG. 7 is a perspective view illustration showing the male component of apparatus in accordance with the present invention.
Figure 8:
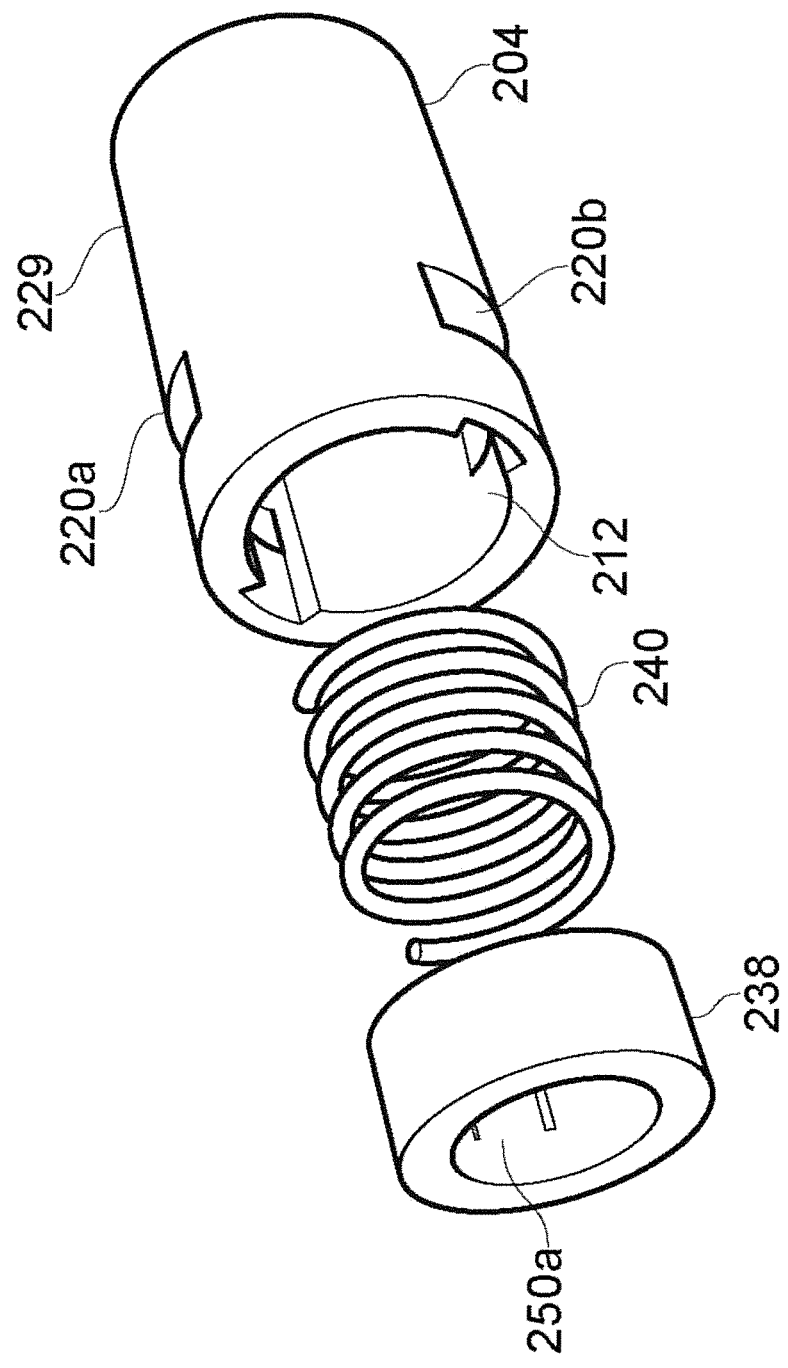
FIG. 8 is an exploded perspective view illustration showing the female component of apparatus in accordance with the present invention.

FIG. 7 is a simple illustration showing that plunger 234 fits into the middle of spring 232 which itself fits into end cap 230. Plunger 234 is also shown as fitting into the cavity 258 of plunger guide 210 of the male component 202. Likewise, FIG. 8 is a simple illustration which in this case shows that spring 240 fits into cavity 212 of the cylinder 229 of female component 204 and collar 238 fits over the end of spring 240 and into cavity 212. A catch member 250a is also partially visible in the figure.

Figure 9:
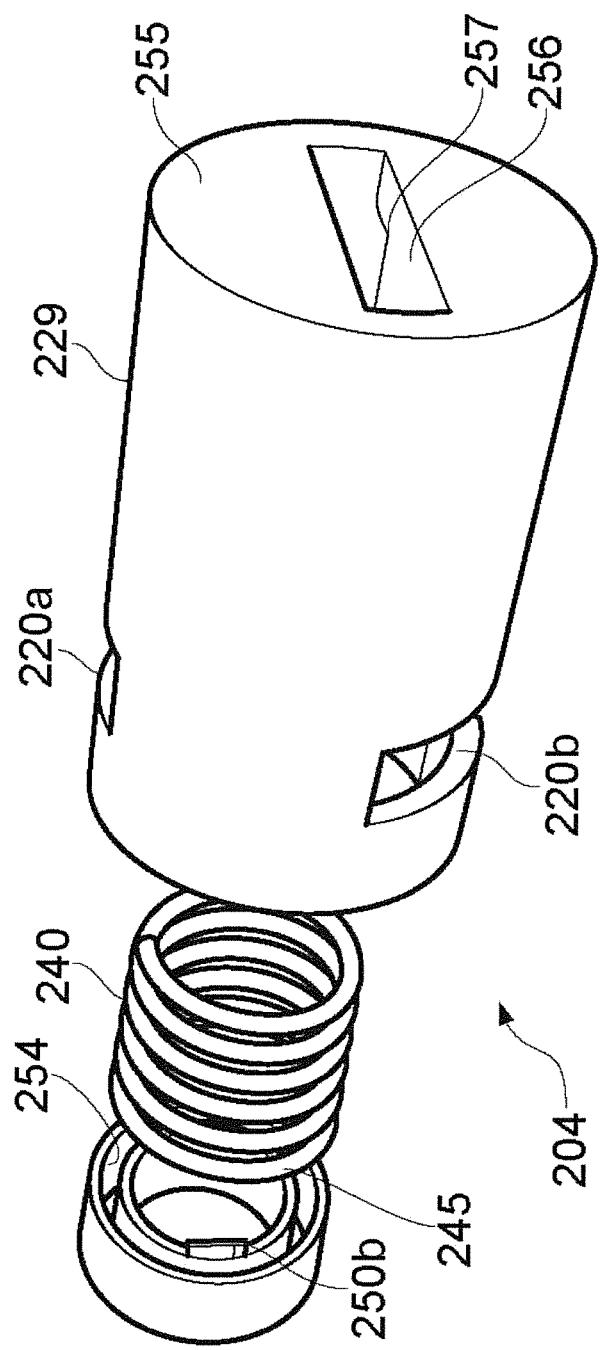
FIG. 9 is an exploded perspective view illustration showing the female component of apparatus in accordance with the present invention from a different aspect.

FIG. 9 illustrates the female component 204 from another perspective clearly showing that the distal end 245 of spring 240 fits into groove 254. Catch member 250b is also partially visible. Also visible is end wall 255 and cavity 256. Also partially visible is a strut 257 which extends from end wall 255 to support stopper 241 (not shown). As can be seen, strut 257 does not extend to the inner side wall of cylinder 229 thereby providing a pathway for liquid from the interior of cylinder 229 to cavity 256.

Figure 10:
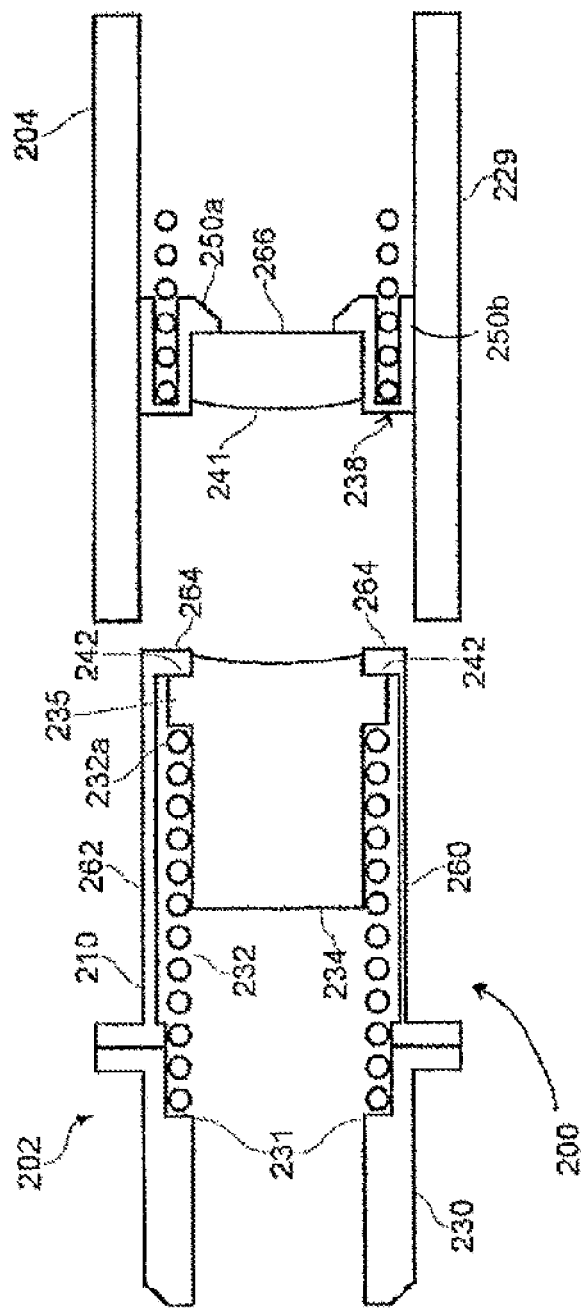
FIG. 10 is a cross-sectional view showing the male and female components of the apparatus of the present invention disposed prior to engagement.

Turning now to FIG. 10, a schematic illustration of a cross-section of valve assembly 200 prior to coupling respective male and female components together shows further respective male and female components assembled and ready for coupling together. Male component 202 has the plunger guide 201 and end cap connected together and spring 232 is compressed such that one end, 232a, abuts shoulder 235 of plunger 234 and the other end abuts an interior formation 231 of the male component 202, in the illustrated case a formation on end cap 230. The compression of spring 232 causes the engagement surface 242 of plunger 234 to be biased against and abut partially inwardly extending portion 264 of the plunger guide 210 side wall. The outer side wall 262 of plunger guide 210 is configured to be in slideable engagement with the inner wall of cylinder 229 when inserted into the female component 202. Also shown is a thinner section 260 of the side wall 262 which forms the bottom of groove 209 illustrated in previous figures.

The female component 204 is assembled and the catch members 250a and 250b of collar 238 are urged into abutment against the rear wall 266 of stopper 241 by biasing action of spring 240 which is entrapped in a structure not visible in the illustrated cross-section. The cross-section view illustrated in FIG. 10 is also from an aspect which does not show the strut 257 extending from the end wall 255 (also not shown) and supporting the stopper 241.

Figure 11:
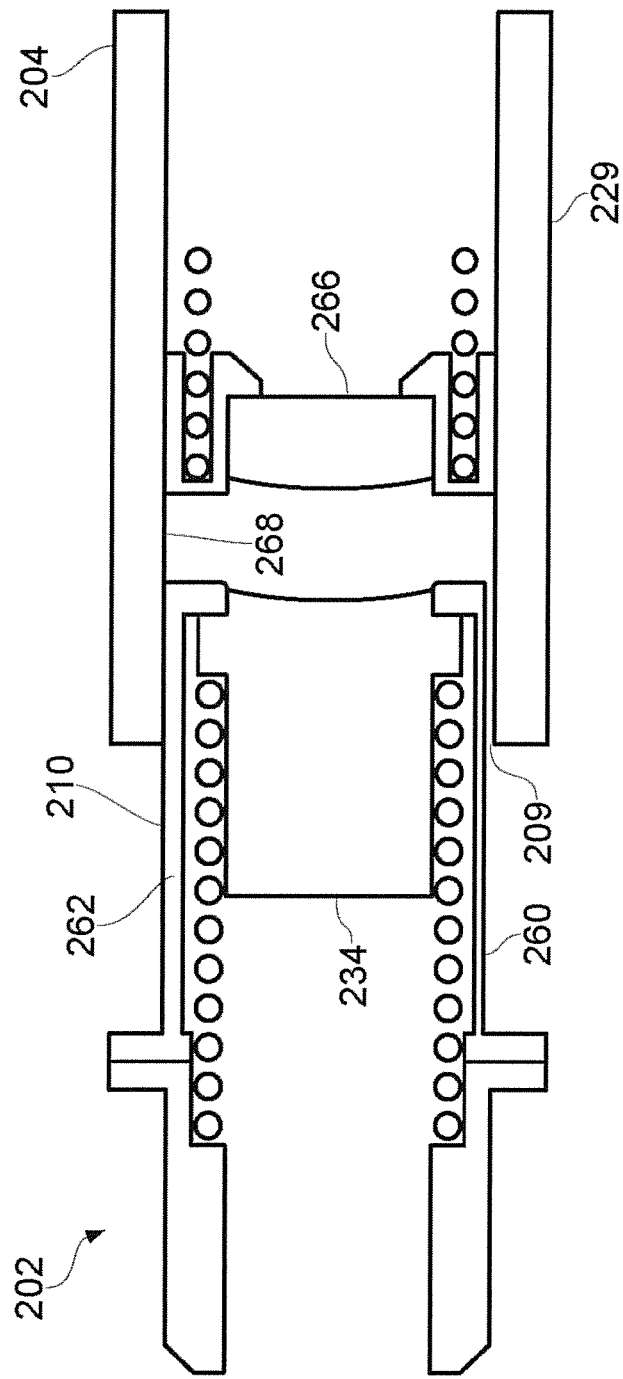
FIG. 11 is a cross-sectional view showing the male and female components of the apparatus of the present invention disposed in an intermediate stage leading to secure and sealed engagement.

FIG. 11 is a schematic illustration of the male component 202 partially inserted into the female component 202. The slideable engagement of plunger guide 210 outer wall 262 with the inner wall 268 of cylinder 229 is clearly illustrated. Additionally, groove 209 can be seen to be in the process of being formed between the thinner portion 260 of the plunger guide wall and the corresponding part of the inner wall of cylinder 229.

Figure 12:
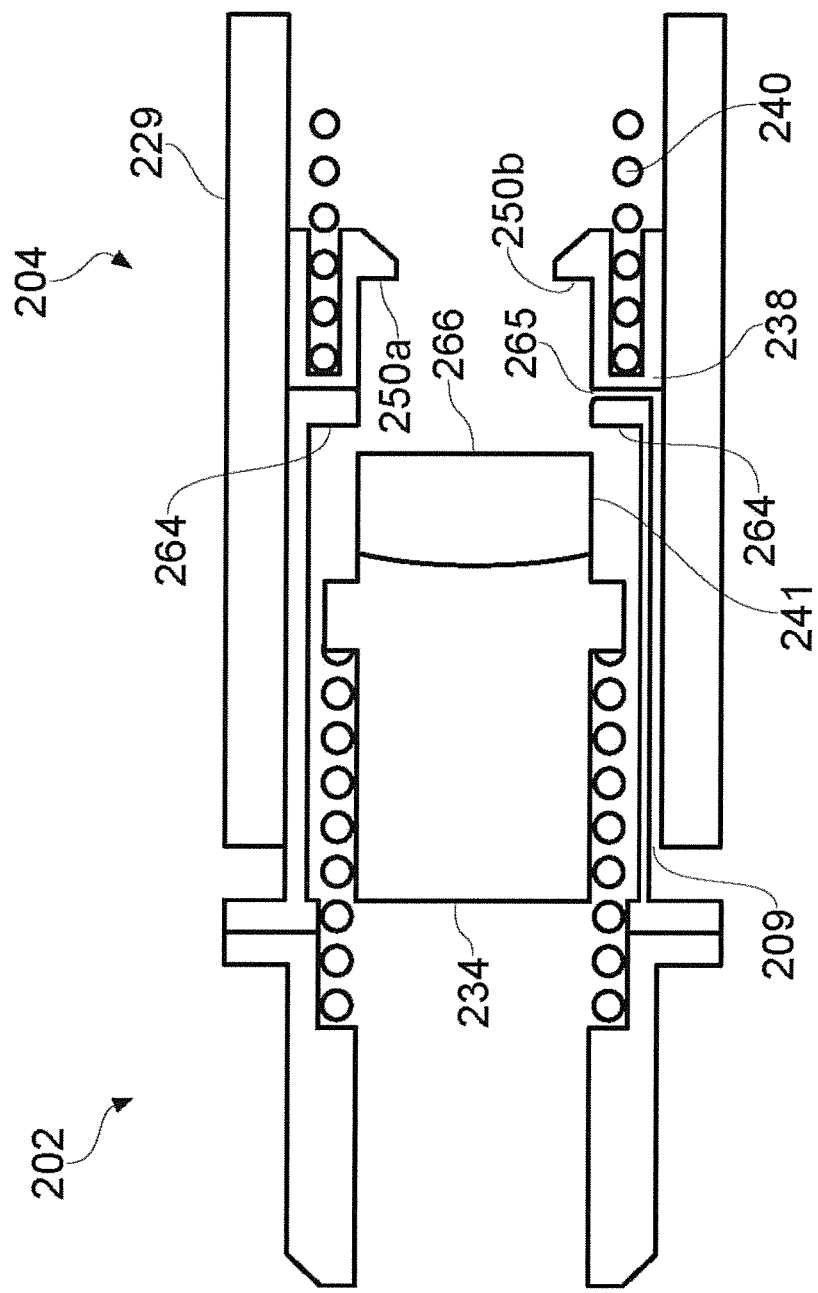
FIG. 12 is a cross-sectional view showing the male and female components of the apparatus of the present invention disposed in secure and sealed engagement illustrating formation of a gas communication pathway and a liquid communication pathway.

FIG. 12 is a schematic illustration on the male component and female component fully engaged with each other. As can be seen, the travel of plunger guide into the cylinder 229 has caused the inwardly extending wall portion 264 to engage with collar 238 and force it back against spring 240. It should be noted that groove 209 extends along the inwardly extending wall 264 in the region 265 to form a gas pathway from groove 209 into the interior of cylinder 229. The gas pathway 265/209 provides a venting mechanism for air to escape from a reservoir being filled with a liquid but also may provide for the ingress of air into a bottle from which the liquid is being supplied to the reservoir.

Figure 13:
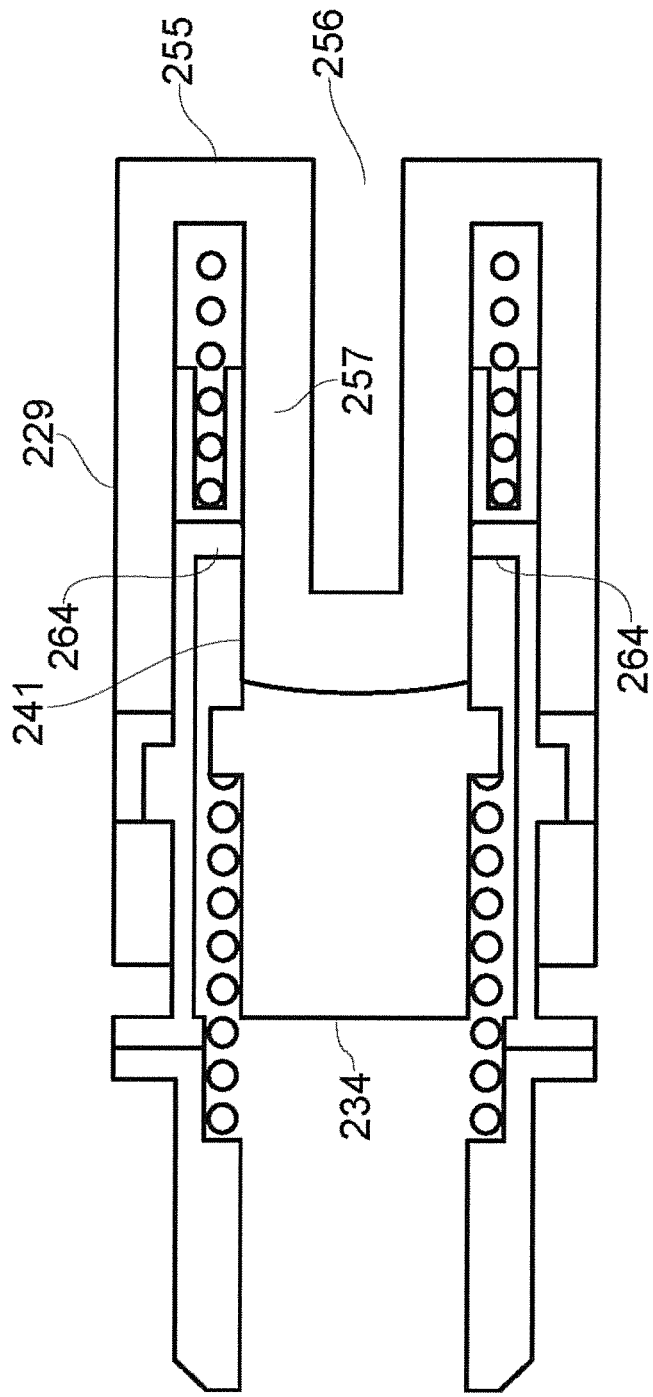
FIG. 13 is a cross-sectional view showing the male and female components of the apparatus of the present invention disposed in secure and sealed engagement from a different aspect.

Stopper 241 engages with plunger 234 to prevent it travelling with the plunger guide 210 and forces it back against spring 232 to open a gap between the male component 202 and the female component 204 thereby opening both the valve element of the male component 202 and the valve element of the female component 204 to provide a liquid pathway between the male and female components. Turning now to FIG. 13, a cross-section is illustrated from a different aspect to that illustrated in FIG. 12 which illustrates the structure and arrangement of cylinder 229 and how stopper 241 is supported. As can be seen from FIG. 13, end wall 255 extends inwardly to form strut 257. Strut 257 is not of continuous tubular form but is discontinuous to allow a liquid to pass around stopper 241 into cavity 256.

Groove 209/265 cannot be seen in FIG. 13 as the groove is narrow and not visible from the aspect from which the cross-section shown in FIG. 13 is viewed.

Figure 14:
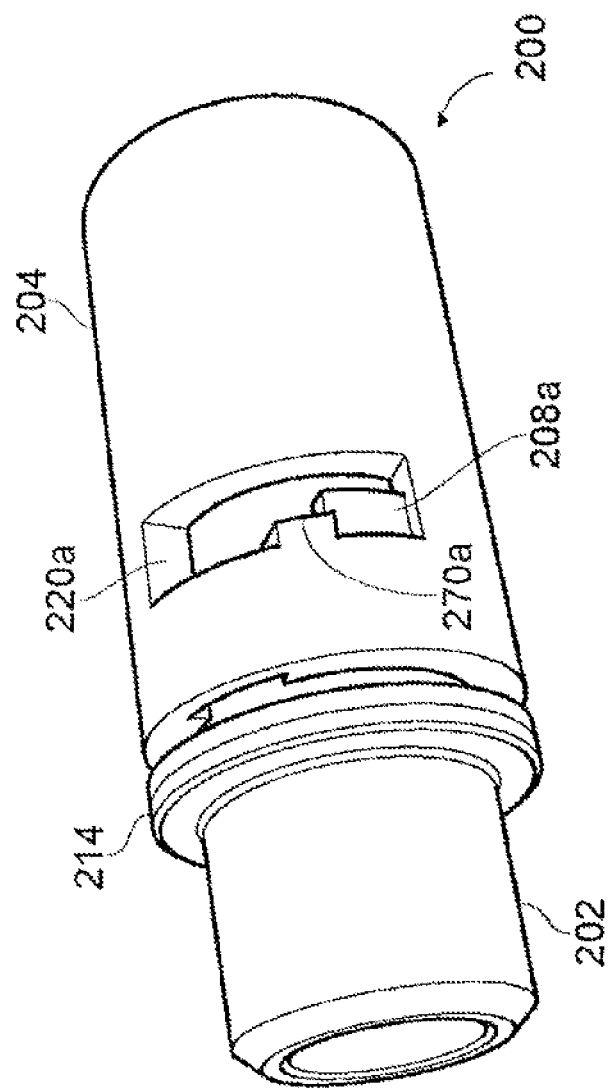
FIG. 14 is a perspective view showing the male and female components of the apparatus of the present invention disposed in an intermediate stage prior to secure and sealed engagement.

FIG. 14 illustrates the locking/coupling arrangement between the male component 202 and female component 204 with reference to slot 220a in an intermediate stage just prior to full locking. As can be seen, slot 220a includes a barrier portion 270a. When plunger guide 210 is inserted into cylinder 229 tongue 208a travels through guide 206a to slot 220a. The material of cylinder 229 and/or tongues 208a and 208b and/or plunger guide 210 may be resiliently deformable, for example the material may be a suitable plastics material. Optionally, the tongues 208a and 208b may be movably biased away from the outer wall of the plunger guide.

Figure 15:
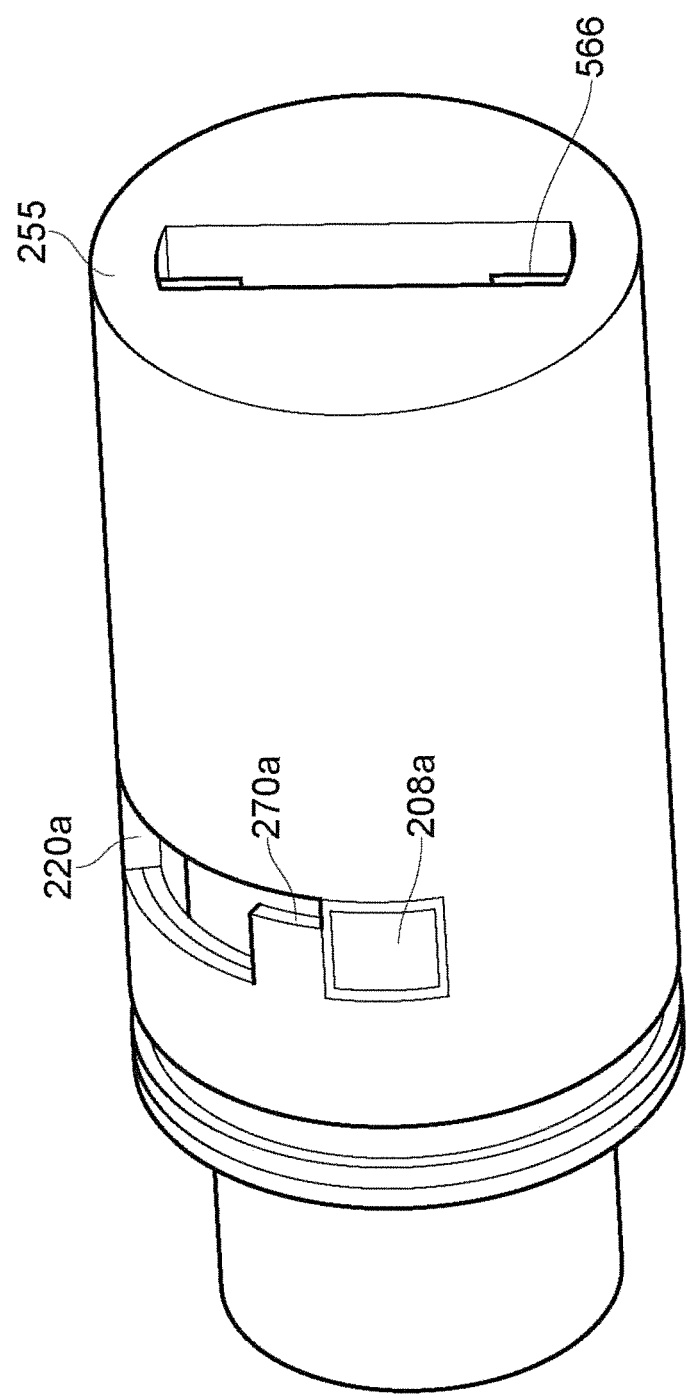
FIG. 15 is a perspective view showing the male and female components of the apparatus of the present invention disposed in a secure and sealed engagement.

When tongue 208a reached slot 220a it engages with the slot and twisting of plunger guide 210/male component 202 and pressure against spring 240 will cause tongue 208a to pass around barrier 270a. Releasing pressure against spring 240 will cause plunger guide 210 to be forced back and behind barrier 270a thereby locking the male component 202 to the female component 204 through the action of the bias of spring 240. Such action may provide a "snap-fit" type of engagement. This makes it relatively difficult to separate the male and female components from each other and inhibits minor separation which would cause leakage of liquid from the valve assembly without closing respective valve elements of the male and female components. FIG. 15 illustrates the locking mechanism when the tongue 208a is fully engaged with slot 220a in the locked position.

Figure 16:
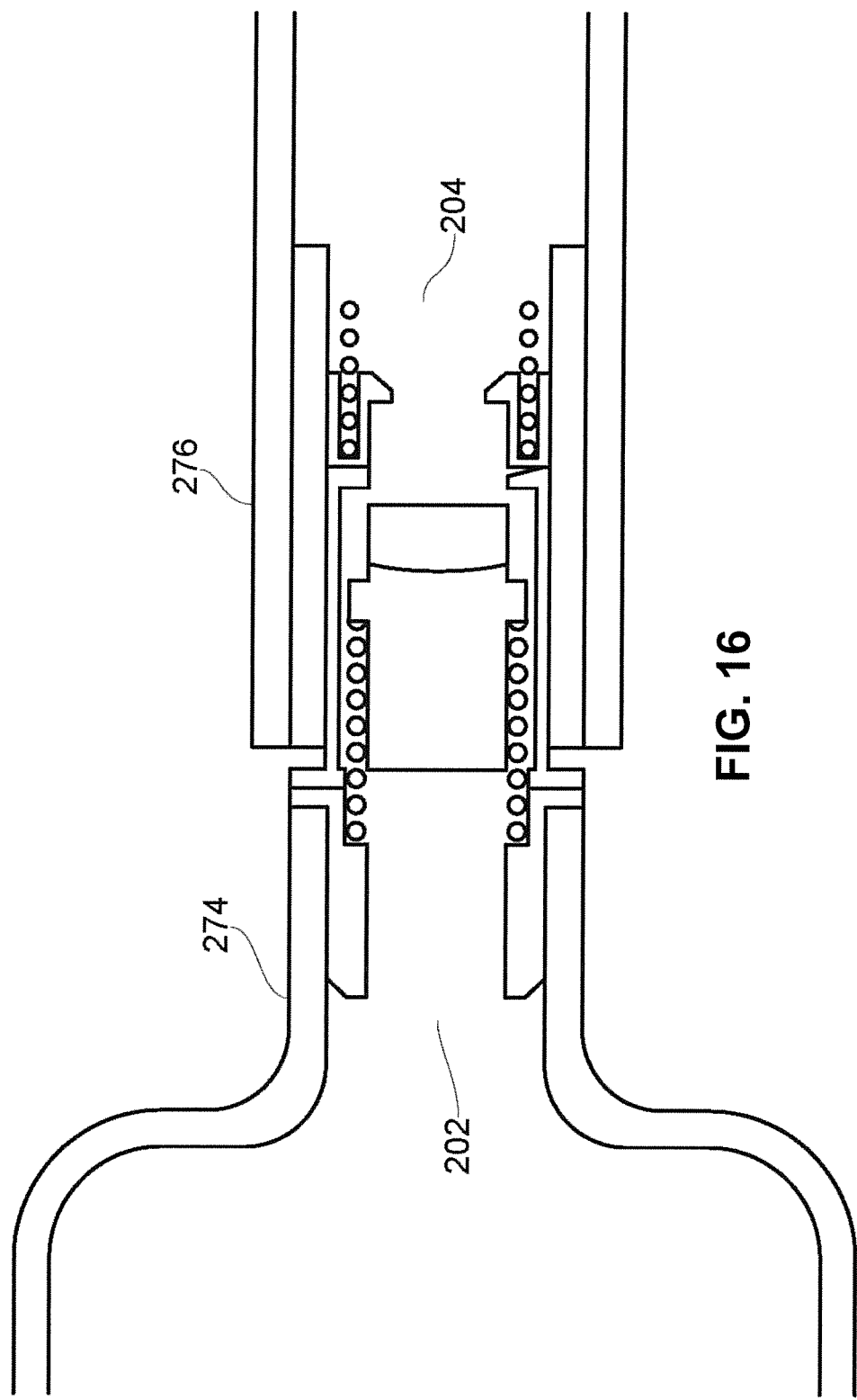
FIG. 16 is a cross-sectional view showing a portion of a dispenser disposed in secure and sealable engagement with a smoking-substitute device.
Figure 17:
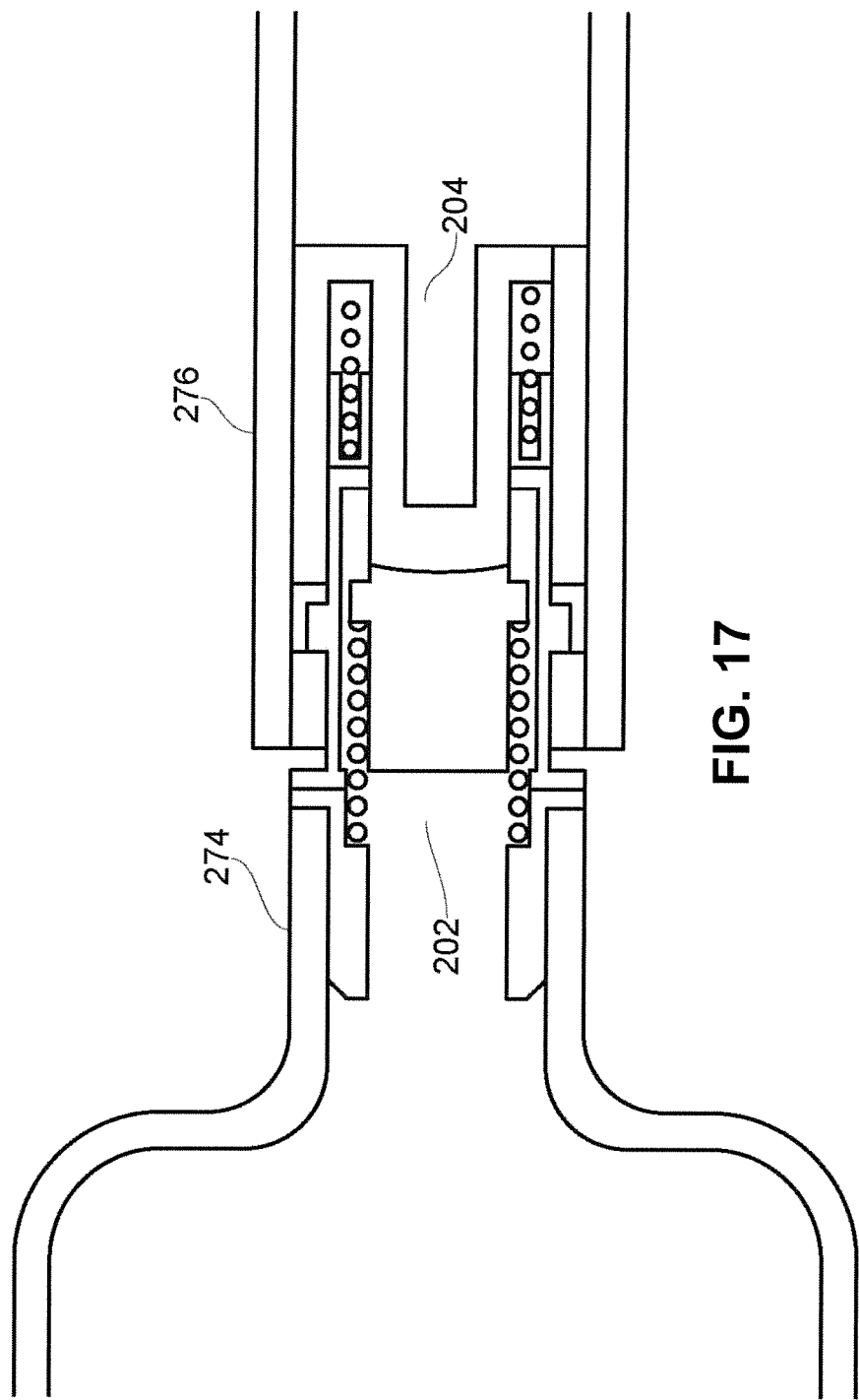
FIG. 17 is a cross-sectional view showing the portion of the dispenser disposed in secure and sealable engagement with the smoking-substitute device from a different perspective.

Turning now to FIG. 16, use of the valve assembly for dispensing liquid from a bottle into the reservoir of an electronic smoking device is illustrated in cross-section. The male component 202 of the valve assembly is disposed in the neck of a liquid dispenser bottle 274. The female component 204 of the valve assembly is disposed in the reservoir of a smoking-substitute device, e.g. e-cigarette, 276. Respective male and female components 202 and 204 are respectively fitted to the neck of dispenser bottle 274 and inlet to the reservoir of the smoking device 276. Before insertion respective valve elements of male and female components 202 and 204 are closed. When the components are inserted one within the other to form the valve assembly they are locked together and respective valve elements opened to permit liquid to flow from dispenser bottle 274 to the reservoir of smoking-substitute device 276. FIG. 17 is an illustration of the arrangement of FIG. 16 but from a different aspect that shows the strut supporting the stopper 241.

The slideable fit between the male and female components 202 and 204 is configured to inhibit flow of liquid and so should be too narrow to encourage a capillary action to draw a liquid between the interface of the outer wall 262 of the male component 202 and the inner wall of the cylinder 229 of the female component 204. In that regard it is not a so-called interference fit but a transitional fit permitting close slideable engagement yet inhibits the flow of liquid.

There has been described in the foregoing one or more embodiments of a smoking-substitute device and refilling apparatus for a substitute-smoking device that avoids or at least ameliorates the problems of the prior art and that addresses the statutory legal requirements that will shortly be implemented in certain markets. More particularly, there is disclosed one or more embodiments of a smoking-substitute device and smoking-substitute device refill apparatus that permits the refilling of a reservoir from a dispenser without, or at least with reduced, leakage or spillage.

As used herein any reference to "one embodiment" or "an embodiment" means that a particular element, feature, structure, or characteristic described in connection with the embodiment is included in at least one embodiment. The appearances of the phrase "in one embodiment" or the phrase "in an embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

In view of the foregoing description it will be evident to a person skilled in the art that various modifications may be made within the scope of the invention. For example, although helical coil springs have been described in the foregoing, embodiments in accordance with the present invention are not limited to using such springs. Other resiliently biased structures may be used such as leaf springs or a resiliently compressible or extendable material. Different configurations of resilient member may be used for respective male and female elements. Additionally, slots 220 need not extend precisely circumferentially but merely transverse to the direction of insertion of the male component into the female component such that movement in the insertion direction is inhibited.

In the described embodiment, helical coil spring 232 has an end distal from the plunger abutting an interior formation 231 of the end cap 230. Optionally, that end of spring 232 may abut the end wall of end cap 230.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. A system for transferring liquid between a dispenser and a reservoir comprising:
    a coupling assembly for securably and sealably engaging said dispenser to said reservoir, the coupling assembly moveable between an unsecured and closed position in which liquid and gas communication is restricted between a dispenser outlet and a reservoir inlet and a reservoir outlet and a dispenser inlet, and a secured and open position in which the coupling assembly opens a liquid communication pathway between said dispenser and said reservoir through the dispenser outlet and reservoir inlet; and
    wherein the coupling assembly opens a gas communication pathway between said reservoir and atmosphere through the reservoir outlet and a vent in the coupling assembly;
    wherein the coupling assembly includes a male component and a female component configured and arranged to be fully engaged with one another, the male component including a plunger guide with an inwardly extending portion at a distal end thereof, and the female component including a cylinder with an inner side wall having a groove extending longitudinally therein, and a collar circumferentially extending within the cylinder;
    the plunger guide configured and arranged to extend into the cylinder, engage the inwardly extending wall portion with the collar, and thereby force the collar back against a spring;
    the gas communication pathway is formed between the inwardly extending portion of the plunger guide and the collar of the female component and extends through the groove in the cylinder of the female component to an external atmosphere.

2. The system according to claim 1, wherein the coupling assembly simultaneously opens said liquid communication pathway; and wherein the vent extends between the male and female components of the coupling assembly, and the female component of the coupling assembly is not the reservoir.

3. The system according to claim 1, wherein the coupling assembly is adapted to close both the liquid communication pathway and the gas communication pathway as it is moved away from the secured position to disengage the dispenser and reservoir.

4. The system according to claim 1, wherein, in the open position, the system is operable to permit liquid to be transferred through the liquid communication pathway, and for a substantially equivalent volume of gas to be expelled through the gas communication pathway.

5. The system as claimed in claim 4, wherein, in the open position, the system is configured and arranged to maintain a substantially equal pressure in the dispenser and reservoir.

6. The system according to claim 1, wherein said dispenser outlet comprises a valve that is actuable when the coupling assembly is secured in the open position to open said liquid communication pathway between said dispenser and said reservoir.

7. The system according to claim 1, wherein said reservoir outlet comprises a valve that is actuable when the coupling assembly is secured in the open position to open said gas communication pathway between said reservoir and dispenser.

8. The system as claimed in claim 7, wherein the valve is biased to close the gas communication pathway when the coupling assembly is not secured in the open position.

9. The system according to claim 1, wherein the coupling assembly comprises a guide assembly for guiding movement of the dispenser outlet into the secured and open position.

10. The system according to claim 1, wherein the coupling assembly comprises a male member, and a female member configured for securely and removably receiving said male member.

11. The system according to claim 1, wherein the coupling assembly comprises a bayonet-type arrangement.

12. A coupling assembly comprising:
a dispenser including a dispenser inlet and dispenser outlet;
a reservoir including a reservoir inlet and a reservoir outlet; and
a coupler positioned between and engaging with the dispenser and the reservoir, the coupler configured to transfer liquid between the dispenser and the reservoir by moving between
an unsecured and closed position in which liquid and gas communication is restricted between the dispenser outlet and the reservoir inlet and the reservoir outlet and the dispenser inlet, and
a secured and open position in which the coupler opens a liquid communication pathway between the dispenser and the reservoir through the dispenser outlet and the reservoir inlet and opens a first gas communication pathway between the reservoir and an atmosphere through the reservoir outlet and a vent in the coupler;
wherein the coupling assembly further includes a male component and a female component configured and arranged to be fully engaged with one another, the male component including a plunger guide with an inwardly extending portion at a distal end thereof, and the female component including a cylinder with an inner side wall having a groove extending longitudinally therein, and a collar circumferentially extending within the cylinder;
the plunger guide configured and arranged to extend into the cylinder, engage the inwardly extending wall portion with the collar, and thereby force the collar back against a spring;
wherein the first gas communication pathway is formed between the inwardly extending portion of the plunger guide and the collar of the female component and extends through the groove in the cylinder of the female component to an external atmosphere.

13. The coupling assembly of claim 12, wherein the female component of the coupling assembly is not the reservoir.

14. The coupling assembly of claim 13, wherein the coupler is further configured to close both the liquid communication pathway and the first gas communication pathway as the coupler is disengaged from the dispenser and the reservoir.

15. The coupling assembly of claim 13, wherein the coupler is further configured in the secured and open position to permit liquid to be transferred through the liquid communication pathway, and for a substantially equivalent volume of gas to be expelled through the first gas communication pathway.

16. The coupling assembly of claim 12, wherein the coupler is further configured in the secured and open position to maintain a substantially equal pressure in the dispenser and the reservoir.

* * * * *